(12) United States Patent
Chak et al.

(10) Patent No.: US 8,834,459 B2
(45) Date of Patent: Sep. 16, 2014

(54) NEEDLE FOR TREATING DISEASES

(76) Inventors: Mark Chak, Brooklyn, NY (US);
Alexander Chak, Brooklyn, NY (US)

( * ) Notice: Subject to any disclaimer, the term of this patent is extended or adjusted under 35 U.S.C. 154(b) by 338 days.

(21) Appl. No.: 13/506,074

(22) Filed: Mar. 26, 2012

(65) Prior Publication Data
US 2013/0253497 A1    Sep. 26, 2013

(51) Int. Cl.
*A61B 18/02* (2006.01)
*A61B 18/00* (2006.01)

(52) U.S. Cl.
CPC ....... *A61B 18/02* (2013.01); *A61B 2018/00714* (2013.01); *A61B 2018/00642* (2013.01); *A61B 2018/0262* (2013.01); *A61B 2018/00791* (2013.01); *A61B 2018/0293* (2013.01); *A61B 2218/007* (2013.01)
USPC .......................................................... 606/21

(58) Field of Classification Search
CPC ............... A61B 18/02; A61B 2018/00041; A61B 2018/00642; A61B 2018/00714; A61B 2018/00791; A61B 2018/0262; A61B 2018/0293; A61B 2218/007
USPC .......................................... 606/20–27, 34, 41
See application file for complete search history.

(56) References Cited

U.S. PATENT DOCUMENTS

| | | | | |
|---|---|---|---|---|
| 4,236,518 A * | 12/1980 | Floyd | .............................. | 606/26 |
| 4,946,460 A * | 8/1990 | Merry et al. | .................... | 606/24 |
| 5,282,799 A * | 2/1994 | Rydell | .............. | 606/48 |
| 6,182,666 B1 * | 2/2001 | Dobak, III | .................... | 128/898 |
| 6,527,765 B2 * | 3/2003 | Kelman et al. | .................. | 606/22 |
| 6,565,556 B1 * | 5/2003 | Korpan et al. | .................. | 606/23 |
| 6,589,234 B2 * | 7/2003 | Lalonde et al. | ................. | 606/23 |
| 6,648,880 B2 * | 11/2003 | Chauvet et al. | ................. | 606/21 |
| 6,736,809 B2 * | 5/2004 | Capuano et al. | ................. | 606/21 |
| 6,890,332 B2 * | 5/2005 | Truckai et al. | .................. | 606/41 |
| 7,393,350 B2 * | 7/2008 | Maurice | ......................... | 606/21 |
| 7,846,154 B2 * | 12/2010 | Bliweis et al. | ................. | 606/24 |
| 2005/0234446 A1 * | 10/2005 | Van Wyk et al. | ............... | 606/41 |

* cited by examiner

*Primary Examiner* — Michael Peffley
*Assistant Examiner* — Daniel Fowler

(57) ABSTRACT

A hollow needle for removing unhealthy inclusions from organism is cooled by filling with a cooling medium by its cooling device and freezes an inclusion, the needle is then heated by it heating device to dislodge the inclusion, and thereafter the dislodged inclusion is withdrawn through a passage in the needle by its withdrawing device.

3 Claims, 1 Drawing Sheet

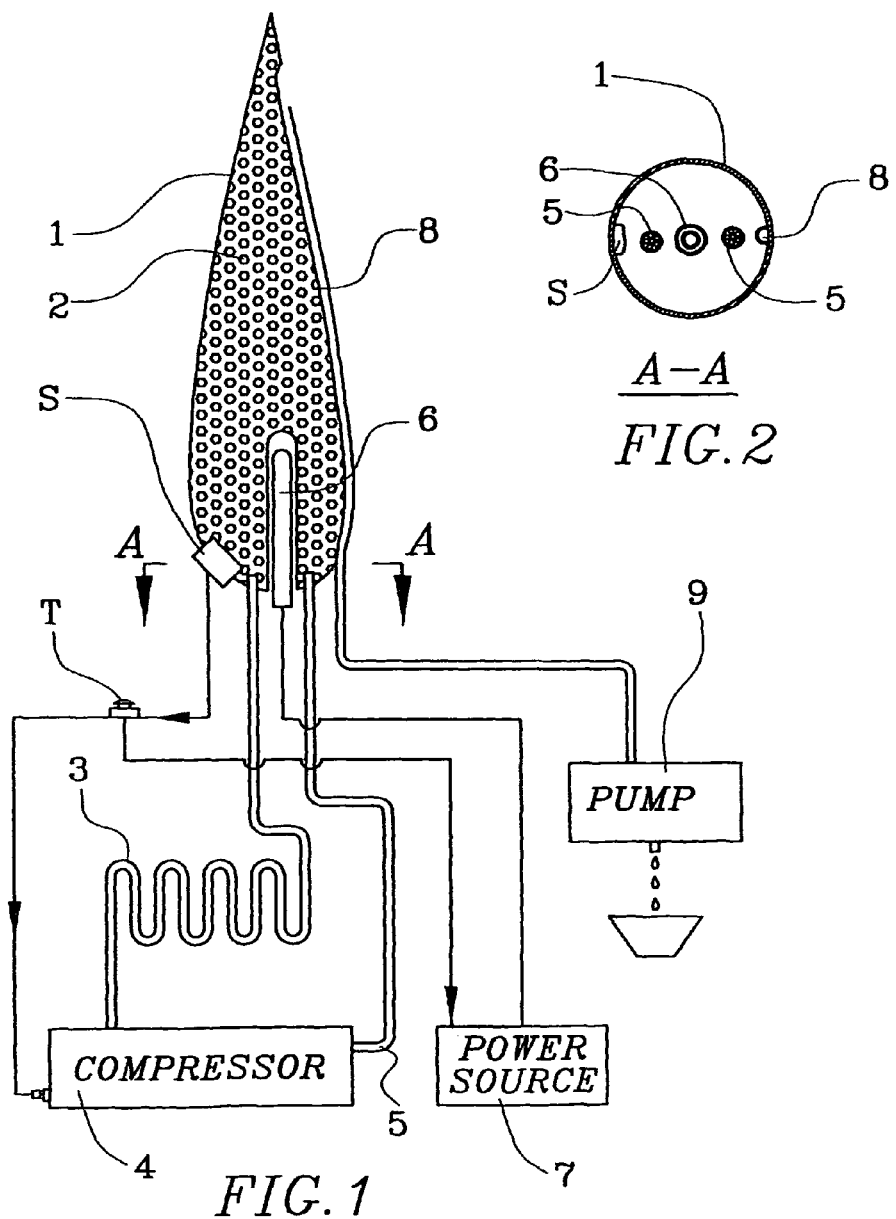

NEEDLE FOR TREATING DISEASES

BACKGROUND OF THE INVENTION

The present invention relates to a needle for treating diseases for example, cancer, aids, polyps, prostate tumors, etc.

More particularly it relates to apparatuses and methods for treating diseases, which use freezing of unhealthy inclusions in an organism.

SUMMARY OF THE INVENTION

Accordingly, it is an object of the present invention to provide a needle for treating diseases for example cancer tumors, aids, polyps, prostate tumors, etc., which is a further improvement of the existing apparatuses.

In keeping with these objects and with others which will become apparent hereinafter, one feature of the present invention resides, briefly stated, in a needle for treating diseases, comprising a hollow needle element having an interior; cooling means supplying a cooling medium into the interior of the hollow needle element and cooling the needle element and thereby freezing an unhealthy inclusion when the hollow needle element filled with the cooling medium is introduced into the unhealthy inclusion; means for heating the needle inserted into the interior of the needle in contact with the hollow needle element and heating the hollow needle element and thereby heating the unhealthy inclusion to dislodge it; and withdrawing means for withdrawing the unhealthy inclusion from an area in which it was frozen and including a withdrawing passage formed in the hollow needle element.

Another feature of the present invention resides, briefly stated, in a recirculating means connected with the cooling means and recirculating the cooling medium through the interior of the hollow needle element, electric source means electrically heating the heating means, and pump means connected with the passage and forcibly evacuation the frozen unhealthy inclusion from the passage outwards of the hollow needle element.

A further feature of the present invention resides in temperature sensing means sensing a temperature of said hollow needle element; means for adjusting a temperature of cooling in a cooling phase in response to a temperature sensed by the sensing means; and means for adjusting a temperature of heating in a heating phase also in response to a temperature sensed by the same sensing means.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 of the drawings is a view showing a needle for treating diseases of the present invention; and FIG. 2 is a view showing a cross-section of the needle for treating diseases of the present invention;

DESCRIPTION OF THE PREFERRED EMBODIMENTS

A needle for treating diseases in accordance with the present invention has a hollow needle element 1 which can be introduced into an organ with an unhealthy inclusion.

A cooling medium, for example Freon 2 is introduced into an interior of the hollow needle element 1 by cooling means including a cooling aggregate 3, a compressor 4 and a recirculating pipe 5. The cooling medium is supplied by the compressor 4 from the aggregate 3 through the pipe 5 into the hollow needle element 1, and the hollow needle element 1 is cooled to a very low temperature. The temperature of the hollow needle element and/or of the cooling medium is sensed by sensing means formed as a sensor S and can be adjusted to a desired temperature by adjusting means formed as a thermostat T. The cooled hollow needle element 1 introduced into an unhealthy inclusion freezes the unhealthy inclusion by subjecting it to a high level of cold in a cooling stage. The cooling medium heated in the needle flows back into the cooling aggregate to be cooled.

The needle is also provided with heating means formed as a heating device 6 which heats the hollow needle element 1 and thereby dislodges the frozen unhealthy inclusion from the area where it was frozen. The heating device 6 is supplied with power from, for example, an electric power source 7. The temperature of the hollow needle element and/or of the heating device is sensed by the sensor S and can be adjusted by the same thermostat T to a desired temperature.

The needle has withdrawing means including a through going passage 8 formed in the hollow needle element and connected with a pump 9. Under the action of the pump 9 the unhealthy inclusion can be withdrawn through the passage from the area when it was located and then outwards.

The hollow needle operates in the following manner:

During a cooling stage the cooling medium 2 is supplied into the interior of the hollow needle element 1 and the hollow needle element 1 cooled by the cooling medium is introduced into an unhealthy inclusion and freezes it. The heating device then heats the hollow needle element and the heated hollow needle element dislodges the frozen unhealthy inclusion from the area where it was located. The dislodged unhealthy inclusion is then withdrawn by the withdrawing means from the area through the throughgoing passage outwards of the needle.

All above-mentioned components required for carrying out of all above stages are provided in the same needle, and all stages (cooling, heating, withdrawing) are carried out by the same needle introduced into the unhealthy inclusion.

It will be understood that each of the elements described above, or two or more together, may also find a useful application in other types of constructions differing from the type described above.

While the invention has been illustrated and described as embodied in a needle for treating diseases, it is not intended to be limited to the details shown, since various modifications and structural changes may be made without departing in any way from the spirit of the present invention.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. A needle for treating diseases, comprising
a hollow needle element having a hollow interior;
a cooling device constructed to supply a cooling medium into the hollow interior and cool the hollow needle element to freeze an unhealthy inclusion when said hollow needle element is filled with the cooling medium and is introduced into the unhealthy inclusion, said cooling device including a fluid pathway communicating with the hollow interior for supplying the cooling medium into the hollow interior and withdrawing the cooling medium from the interior, said fluid pathway constructed as a recirculating fluid pathway including a supply pipe portion for introducing the cooling medium into the hollow interior and a withdraw pipe for withdrawing the cooling medium from the hollow interior, wherein the supply pipe and the withdraw pipe are spaced apart;

a heating device inserted into the hollow interior between said supply pipe and said withdraw pipe, in contact with the hollow needle element and constructed to heat the hollow needle element and thereby to heat the unhealthy inclusion to dislodge the unhealthy inclusion; and a withdrawing device constructed to withdraw the unhealthy inclusion from an area it was frozen by the cooling device and dislodged by the heating device and including a withdrawing passage provided on a periphery of the hollow needle element within the hollow interior.

2. A hollow needle for treating diseases according to claim 1, wherein said recirculating fluid pathway recirculates the cooling medium through the hollow interior, and said cooling device further includes a cooling aggregate and a compressor supplying the cooling medium from the cooling aggregate into the recirculating fluid pathway, wherein said heating device is provided with power from an electric power source, and wherein said withdrawing device includes a pump connected with the withdrawing passage and evacuating the frozen unhealthy inclusion outwards of the hollow needle element.

3. A hollow needle for treating diseases according to claim 1, further comprising a sensor constructed to sense a temperature of the hollow needle element and a thermostat which receives a temperature information from the sensor and adjusts the heating device and the cooling device to produce a desired temperature in the hollow needle element.

* * * * *